(12) United States Patent
Kumar

(10) Patent No.: US 8,722,403 B2
(45) Date of Patent: May 13, 2014

(54) SPECIMEN PRESERVATION CHAMBER AND METHOD

(75) Inventor: Sanjay S. Kumar, Tallahassee, FL (US)

(73) Assignee: Florida State University Technology Transfer Office, Tallahassee, FL (US)

( * ) Notice: Subject to any disclaimer, the term of this patent is extended or adjusted under 35 U.S.C. 154(b) by 0 days.

(21) Appl. No.: 13/353,914

(22) Filed: Jan. 19, 2012

(65) Prior Publication Data

US 2012/0184034 A1    Jul. 19, 2012

Related U.S. Application Data

(60) Provisional application No. 61/434,008, filed on Jan. 19, 2011.

(51) Int. Cl.
*A01N 1/00* (2006.01)

(52) U.S. Cl.
USPC .......... 435/374; 435/1.2; 435/1.1; 435/284.1

(58) Field of Classification Search
USPC .................. 435/374, 284.1, 1.1, 1.2, 325
See application file for complete search history.

(56) References Cited

PUBLICATIONS

Krimer, Leonid S., and Goldman-Rakic, Patricia S., An interface holding chamber for anatomical and physiological studies of living brain slices. Journal of Neuroscience Methods 75 (1997) pp. 55-58.*
Brain Slice Chamber System BSC1. Datasheet [online]. Scientific Systems Designs Inc., 1997 [retrieved on Mar. 13, 2013]. Retrieved from the Internet: <URL: http://www.autom8.com/pdfs/brainslice/Manual_BSC1.pdf>.*
Three, Four, or Six Channel Brain Slice Chamber BSC3. Datasheet [online]. Scientific System Design Inc., 1997 [retrieved on Mar. 13, 2013]. Retrieved from the Internet: <URL: http://www.scisys.info/products/bsc3p.html>.*

* cited by examiner

*Primary Examiner* — Jon P Weber
*Assistant Examiner* — Kara Johnson
(74) *Attorney, Agent, or Firm* — J. Wiley Horton

(57) ABSTRACT

The present invention comprises a specimen preserver. A bubble reservoir is used to hold a preserving liquid such as artificial cerebrospinal liquid (aCSF). Oxygen is introduced into the aCSF by a gas diffuser which is attached to the bubble reservoir. The tissue samples are contained in one or more chambers in a holding platform. The platform is suspended well above the bottom of the bubble reservoir. The lower portion of each of the chambers is open toward the bottom of the bubble reservoir, but is covered by a fine mesh. The gas introduced into the aCSF circulates within the bubble reservoir. However, the tissue samples are not directly exposed to the gas bubbles because the fine mesh excludes the bubbles from the chambers in which the tissue samples are housed.

20 Claims, 3 Drawing Sheets

SPECIMEN PRESERVATION CHAMBER AND METHOD

CROSS-REFERENCES TO RELATED APPLICATIONS

This application is a non-provisional application claiming the benefit of an earlier filed provisional application pursuant to the provisions of 37 C.F.R. §1.53 (c). The provisional application was filed on Jan. 19, 2011. It listed the same inventors and was assigned Ser. No. 61/434,008.

STATEMENT REGARDING FEDERALLY SPONSORED RESEARCH OR DEVELOPMENT

None.

MICROFICHE APPENDIX

Not Applicable

BACKGROUND OF THE INVENTION

1. Field of the Invention

This invention relates to the fields of biology and neuroscience. More specifically, the invention comprises a device and method for preserving tissue samples such as brain tissue.

2. Description of the Related Art

Many laboratories use acute brain slices for physiological research. These samples are particularly useful for neurophysiological research directed toward understanding human diseases such as Alzheimer's. Parkinson's, and epilepsy. Such work relies on the health/viability of cut slices of brain tissue to gather crucial physiological and pharmacological data using, electrophysiological techniques.

The preservation of brain tissue samples has proven to be particularly difficult owing to the ephemeral nature of the tissue. Adult brain tissue is particularly susceptible to rapid degradation. It is therefore desirable to provide a device and method which can prolong the viability of tissue samples such as brain tissue samples. A method which can preserve such samples for 6-8 hours after sectioning is needed. The present invention provides such a device and method.

BRIEF SUMMARY OF THE INVENTION

The present invention comprises a specimen preserver with two independent components. These are: (1) a liquid-filled bubble reservoir which contains a gas-infused preserving liquid; and (2) a holding platform including one or more chambers configured to retain a biological specimen. The bubble reservoir is used to hold a preserving liquid such as artificial cerebrospinal liquid (aCSF). Oxygen is typically introduced into the aCSF by a gas diffuser which is submerged within the reservoir.

The holding platform has a top surface and a bottom surface. One or more passages pass vertically through the holding platform, with each passage preferably having a top opening and a bottom opening. The bottom opening is covered by a fine mesh. The combination of a passage and the mesh covering its bottom opening creates a chamber which is open at the top. A biological sample is placed in the chamber.

The platform is suspended well above the bottom of the bubble reservoir. The preserving liquid in the reservoir is filled to a level which is above the bottom surface of the holding platform but below the top surface of the holding platform. The oxygen introduced into the preserving liquid circulates within the reservoir. However, the biological specimens are not directly exposed to the gas bubbles because the fine mesh excludes the bubbles from the bottom opening of each chamber and the top opening of each chamber is above the level of the liquid within the reservoir.

The holding platform provides sturdy support for the slices and minimizes the effects of unintentional mechanical disturbances either through movement or turbulence within the chamber caused by changes in gas pressure.

Figure 1:
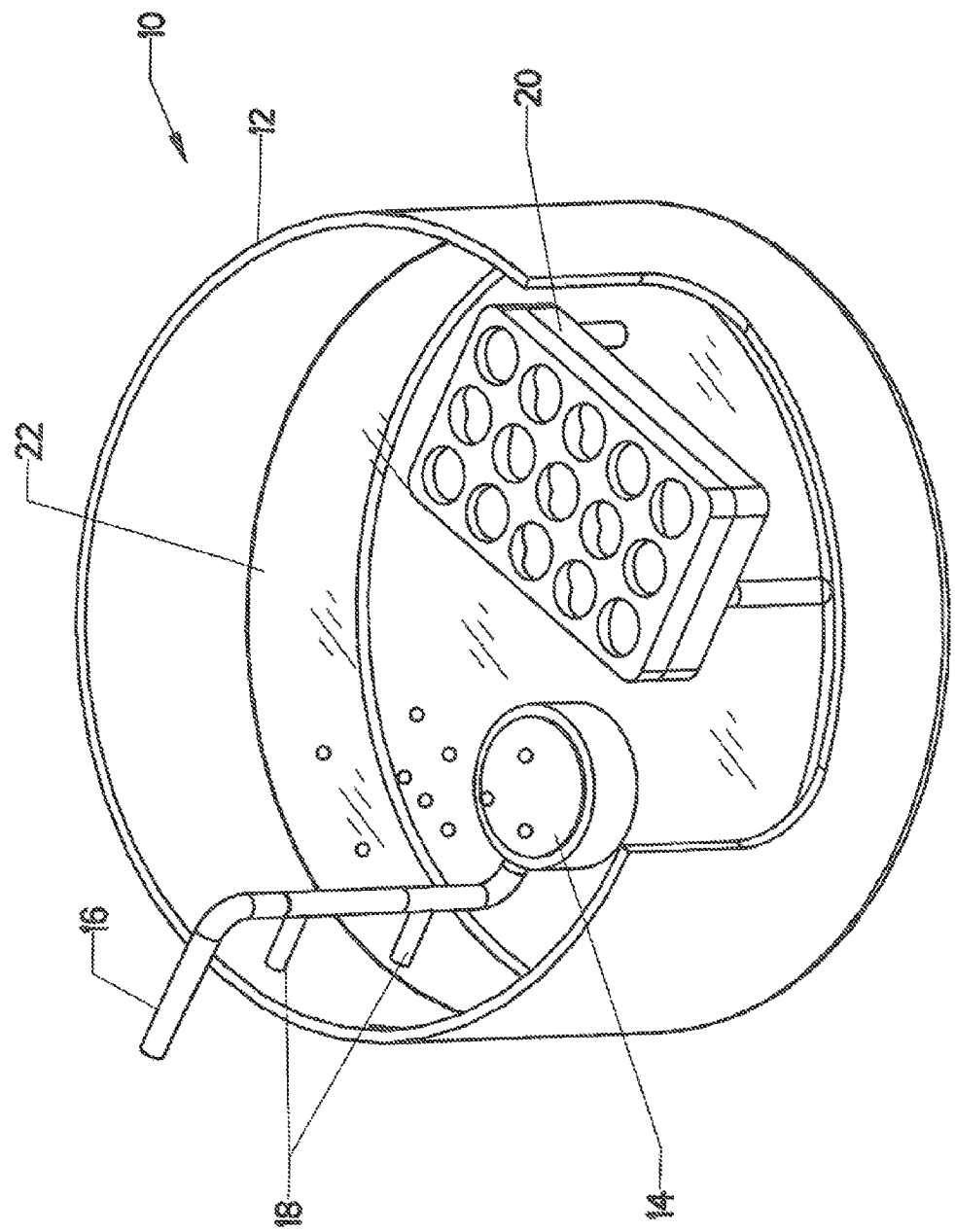
FIG. 1 is a perspective view, showing the components of the present invention.

| REFERENCE NUMERALS IN THE DRAWINGS | | | |
|---|---|---|---|
| 10 | specimen preserver | 12 | bubble reservoir |
| 14 | gas diffuser | 16 | gas inlet pipe |
| 18 | connection | 20 | holding platform |
| 22 | aCSF | 24 | standoff |
| 26 | opening | 28 | screen |
| 30 | sample | 32 | chamber |
| 34 | bottom wall | 36 | side wall |
| 38 | lip | 40 | body |

DETAILED DESCRIPTION OF THE INVENTION

The specimen preserving device and method described herein is adaptable to many applications. However, the preferred embodiment is particularly suited to the preservation of sliced samples of brain tissue, and this exemplary embodiment will be used throughout the following description. FIG. 1 shows the components of the invention. Specimen preserver 10 includes bubble reservoir 12 containing a volume of a preserving liquid. As the embodiment illustrated is intended to preserve brain tissue, the preserving liquid is artificial cerebrospinal liquid (aCSF).

Holding platform 20 is provided to house the brain tissue samples. It is partially immersed in aCSF 22. Gas diffuser 14 is fed by gas inlet pipe 16. The gas diffuser is preferably connected to chamber 12, such as by a pair of connections 18. Gas fed into gas inlet pipe 16 emerges from gas diffuser 14 as a cloud of small bubbles. For the preservation of brain tissue, the gas used is preferably a mixture of oxygen and carbon dioxide. The preferred mixture comprises about 95% oxygen and about 5% carbon dioxide.

Figure 2:
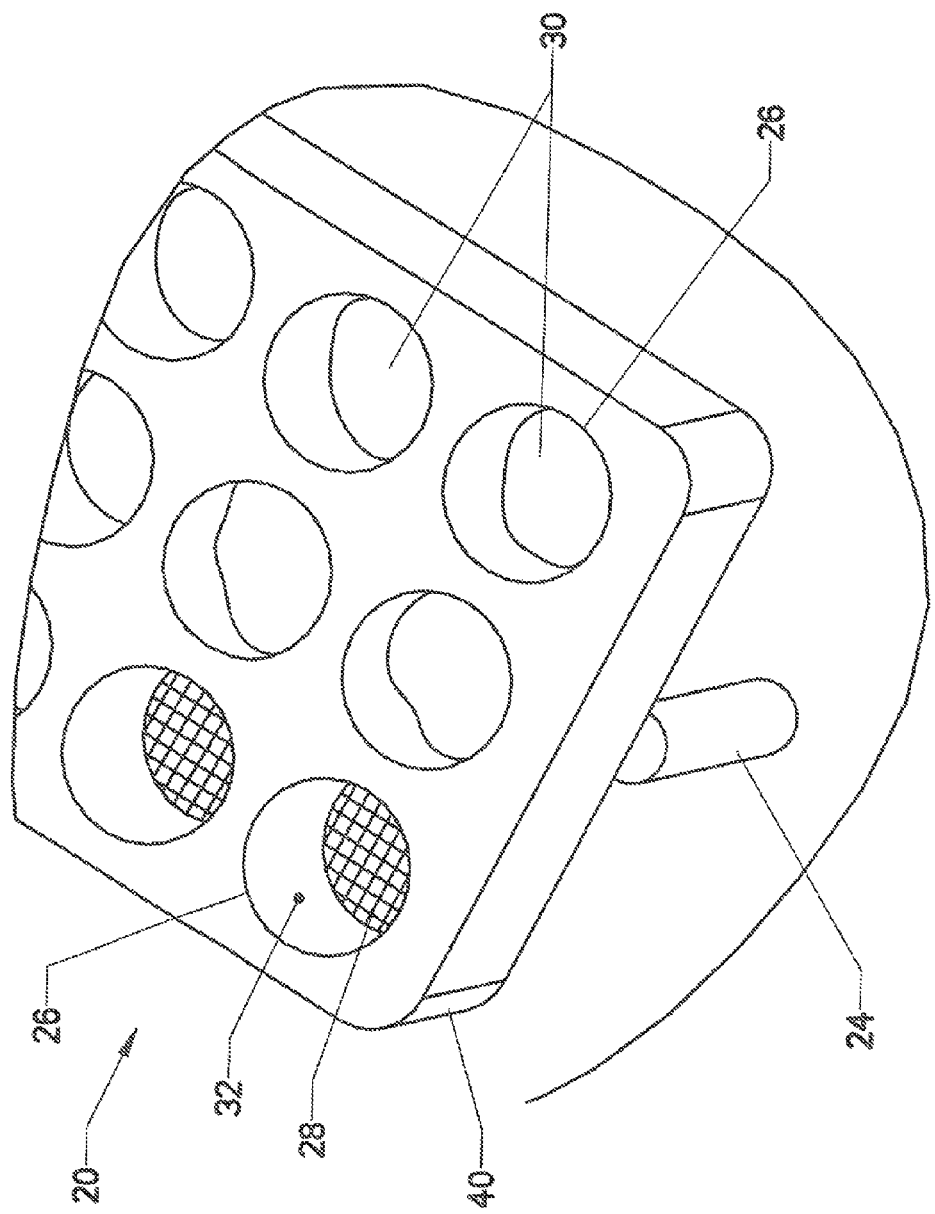
FIG. 2 is a detailed perspective view, showing the holding platform.

FIG. 2 shows a detailed perspective view of holding platform 20. Body 40 is separated from the bottom of bubble reservoir 12 by one or more vertical standoffs 24. The upper surface of body 40 contains a series of openings 26. Each opening defines a vertical passage passing through body 40 from top to bottom. The bottom of each passage is covered by a screen 28. A series of chamber 32 are thus defined. A sample 30 (such as a brain tissue slice) may be placed in each chamber 32.

Figure 3:
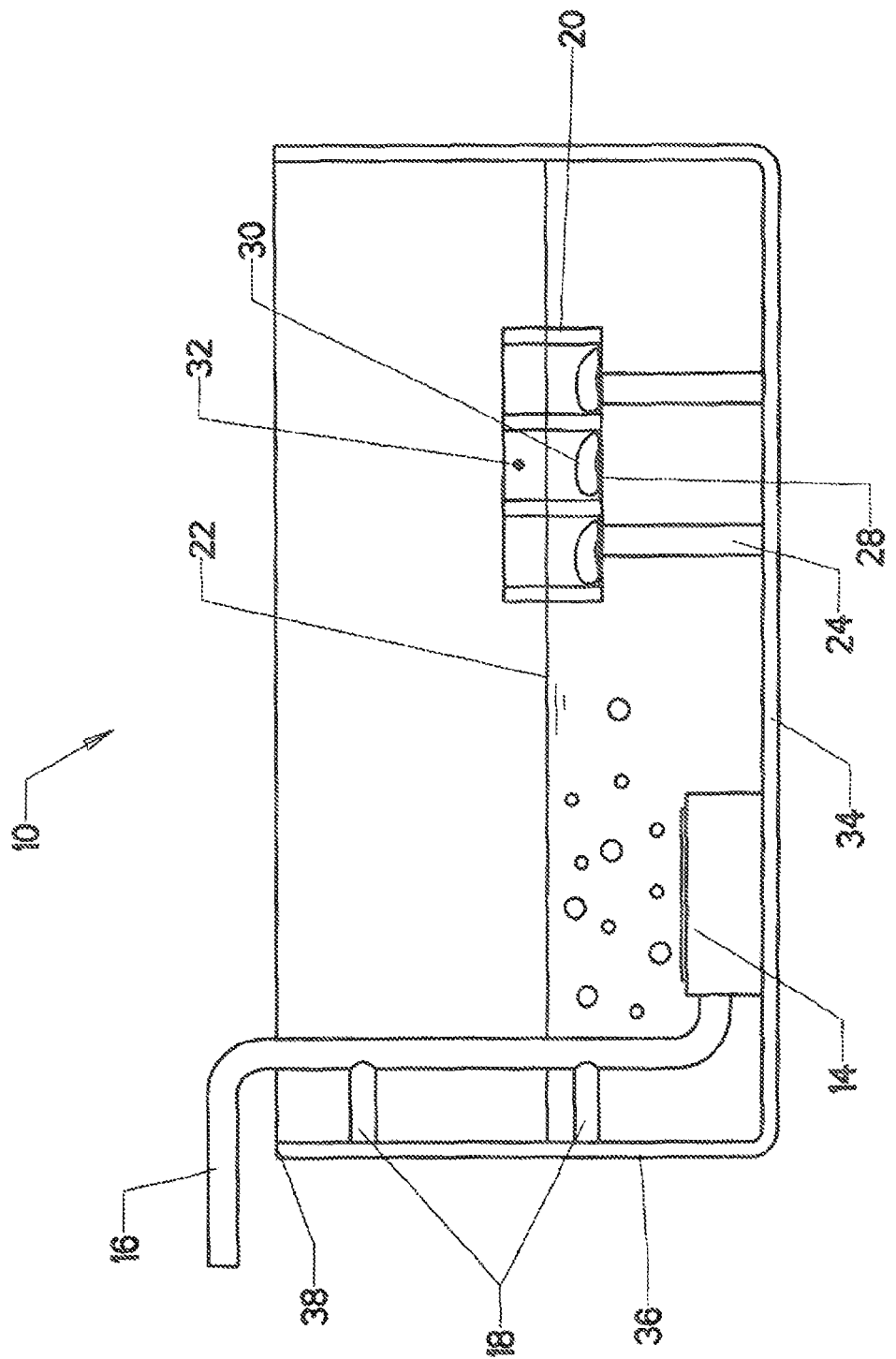
FIG. 3 is an elevation view, showing the invention in operation.

FIG. 3 shows an elevation view of the device in operation. Holding platform 20 and gas diffuser 14 are contained within bubble reservoir 12. The outlet of the gas diffuser is placed well below the surface of aCSF 22. The level of aCSF within the bubble reservoir is significant to the proper operation of the invention. The reader will note that the surface of the aCSF is about midway between the top surface and bottom surface of holding platform 20. This configuration allows samples 30 to rest on screen 28—submerged in aCSF—within the chambers 32 with no fear of the samples floating free of the chambers that contain them. The upper portion of the holding platform also creates a physical barrier which prevents the bubbles entering the top of the specimen chambers. As described previously, screens 28 cover the bottom of each chamber and thereby prevent the unwanted entry of gas bubbles.

Tissue samples 30 rest within the chambers 32 of holding platform 20. Contact between the gas bubbles and the tissue is harmful to the tissue's continued viability and is therefore to be avoided. On the other hand, the tissue actually needs contact with oxygenated aCSF (meaning aCSF with dissolved oxygen) in order to remain viable. The size of the mesh used for screens 28 is preferably selected to meet these dual objectives. The mesh size must be (1) small enough to exclude the smallest bubble which is reasonably expected from the diffuser; and (2) large enough to permit the free passage of oxygenated aCSF.

The location of holding platform 20 and diffuser 14 are preferably selected to minimize the likelihood of free gas bubbles existing directly beneath the holding platform. The location of gas diffuser. 14 is preferably fixed relative to reservoir 12 by providing secure attachment features—such as a pair of connections 18. The gas diffuser could be attached to the bubble reservoir in many other ways. As one example, a connection could be made between gas inlet pipe 16 and lip 38 of bubble reservoir 12. The attachment of the diffuser to the bubble reservoir eliminates the need for adjusting and aligning the diffuser within the bubble reservoir.

In operation, the pressurized gas mixture is fed into gas inlet pipe 12. This emerges as a cloud of small bubbles from gas diffuser 14. The bubbles swirl and mix the artificial cerebrospinal fluid 22—thereby oxygenating it. Tissue samples 30 rest securely at the bottom of the chambers 32 in holding platform 20. The screen 28 closing the bottom of each chamber allows oxygenated aCSF to circulate around the tissue sample. Securing the gas inlet pipe and diffuser to the reservoir helps prevent unwanted contact between these components and the holding platform (as well as unwanted placement of the gas diffuser directly beneath the holding platform).

The gas diffuser produces bubbles having a range of size (from a maximum diameter to a minimum diameter). As explained previously, the mesh size chosen to cover the bottom of the specimen chambers is preferably small enough to exclude the minimum bubble diameter. The preserving liquid will contain dissolved gasses and these dissolved gasses are freely able to circulate through the chambers within the holding platform. Only the undissolved bubbles are excluded.

The holding platform provides support for the tissue samples and minimizes the effects of mechanical disturbances resulting from movement of the chamber or turbulence within the chamber. The open bubble reservoir and relatively large volume of the bubble reservoir (preferably 200 ml to 1000 ml and even more preferably 400-500 ml) also buffers against such disturbances. The configuration of the chambers within the holding platform protects and preserves each tissue sample without compromising its oxygenation.

The holding platform is designed to be placed in the bubble reservoir and removed from the bubble reservoir as a unit. Thus, a battery of tissue samples can be loaded into the holding platform and then placed in the bubble reservoir. The user will position the holding platform so that it does not lie directly over gas diffuser 14.

While the specific parameters used in the exemplary embodiment are in no way to be viewed as limiting the scope of the invention, the reader may gain some benefit from an explanation of these parameters. The preferred mesh size will of course depend upon the size of the bubbles produced by the diffuser, with the goal being for the mesh size to be small enough to exclude the smallest bubble size which is likely to be produced by the diffuser. A preferred mesh size is an opening of 0.50 mm by 0.50 mm (0.0197 inch by 0.0197 inch). Given the composition of the aCSF, the preferred range of mesh sizes is between 0.10 mm and 0.70 mm.

While the invention is not limited to any particular linear dimension or volume, a holding platform size of about 9.5 cm in length by about 5.5 cm in width by about 1.5 cm in height has performed well. In this version the standoffs were positioned to place the mesh screens about 2.5 cm off the bottom wall of bubble reservoir 12. The diameter of each opening 26 is preferably between about 0.5 cm and about 1.5 cm. The openings are shown in the drawing views as being circular, but some embodiments may utilize rectangular openings or other shapes.

In the illustrated embodiments the mesh covers the bottom opening of each chamber. It is also possible to locate the mesh somewhat higher within the chamber. However, as covering the bottom opening is the easiest installation, it has been illustrated.

The material selected for each of the components is not critical to the successful operation of the invention, so long as the material does not compromise the objective of preserving the biological specimens. In the preferred embodiments, bubble reservoir 12 is made of glass. Holding platform 20 is made of a polycarbonate block. Standoffs 24 are made of polycarbonate while connections 18 are made of glass. The screen mesh used to close the bottom of each specimen chamber is preferably made of polypropylene. Various other materials could be substituted, so long as the goal of compatibility with the specimens is maintained.

The reader will thereby appreciate that the present invention proposes a new device and method for preserving tissue samples such as brain tissue slices. The foregoing description and drawings comprise illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention.

Having described my invention, I claim:

1. A method of biological specimen preservation for preserving a biological specimen, comprising:
   a. providing a bubble reservoir having a bottom wall and an open top;
   b. providing a holding platform having a top, a bottom, and at least one chamber passing through said holding platform from said top to said bottom, with said at least one chamber including a top opening and a bottom opening;
   c. locating said holding platform in said bubble reservoir with said bottom of said holding platform being separated from said bottom wall, thereby defining a space lying between said bottom of said holding platform and said bottom wall;
   d. providing a gas diffuser in said bubble reservoir, said gas diffuser lying outside said space lying between said bottom of said holding platform and said bottom wall;

e. covering said bottom opening of said at least one chamber with a screen;
f. filling said bubble reservoir with a preservation liquid to a level above said bottom of said holding platform but below said top of said holding platform, thereby flooding said at least one chamber to a level above said screen;
g. placing said biological specimen in said at least one chamber, said biological specimen having a density greater than said preservation liquid so that said biological specimen sinks to said screen covering said bottom of said at least one chamber;
h. said level of said preservation liquid being sufficient to completely submerge said biological specimen;
i. forcing a gas including oxygen through said gas diffuser, thereby producing a plurality of gas bubbles in said preservation liquid, with said plurality of gas bubbles having a maximum bubble diameter and a minimum bubble diameter; and
j. wherein said screen has a mesh size small enough to prevent the passage of said minimum bubble diameter.

2. A method of biological specimen preservation as recited in claim 1, wherein said mesh size is between about 0.10 mm and about 0.70 mm.

3. A method of biological specimen preservation as recited in claim 2, wherein said mesh size is about 0.50 mm.

4. A method of biological specimen preservation as recited in claim 1, wherein said gas contains about 95% oxygen and about 5% carbon dioxide.

5. A method of biological specimen preservation as recited in claim 1, wherein:
a. said holding platform includes a plurality of chambers passing through said holding platform from said top to said bottom, with each of said chambers including a top opening and a bottom opening; and
b. covering said bottom open of each of said plurality of chambers with a screen.

6. A method of biological specimen preservation as recited in claim 1, further comprising attaching said gas diffuser to said bubble reservoir.

7. A method of biological specimen preservation as recited in claim 1, further comprising attaching said holding platform to said bubble reservoir.

8. A method of specimen preservation for preserving a biological specimen, comprising:
a. providing a bubble reservoir having a bottom wall and an open top;
b. providing a holding platform having a top, a bottom, and at least one chamber passing through said holding platform from said top to said bottom, with said at least one chamber including a top opening and a bottom opening;
c. said holding platform including a standoff for separating said bottom of said holding platform from said bottom wall of said bubble reservoir;
d. covering said bottom opening of said at least one chamber with a screen;
e. filling said bubble reservoir with a preservation liquid to a level above said bottom of said holding platform but below said top of said holding platform, thereby flooding said at least one chamber to a level above said screen;
f. placing said biological specimen in said at least one chamber, said biological specimen having a density greater than said preservation liquid so that said biological specimen sinks to said screen covering said bottom of said at least one chamber;
g. said level of said preservation liquid being sufficient to completely submerge said biological specimen;
h. forcing a gas including oxygen into said preservation liquid in said bubble reservoir, thereby producing a plurality of gas bubbles in said preservation liquid; and
i. wherein said screen has a mesh size small enough to prevent the passage of said plurality of gas bubbles.

9. A method of biological specimen preservation as recited in claim 8, wherein said mesh size is between about 0.10 mm and about 0.70 mm.

10. A method of biological specimen preservation as recited in claim 9, wherein said mesh size is about 0.50 mm.

11. A method of biological specimen preservation as recited in claim 8, wherein said gas contains about 95% oxygen and about 5% carbon dioxide.

12. A method of biological specimen preservation as recited in claim 8, wherein:
a. said holding platform includes a plurality of chambers passing through said holding platform from said top to said bottom, with each of said chambers including a top opening and a bottom opening; and
b. covering said bottom open of each of said plurality of chambers with a screen.

13. A method of biological specimen preservation as recited in claim 8, further comprising attaching said gas diffuser to said bubble reservoir.

14. A method of biological specimen preservation as recited in claim 8, further comprising attaching said holding platform to said bubble reservoir.

15. A method of biological specimen preservation for preserving a biological specimen, comprising:
a. providing a bubble reservoir having a bottom wall and an open top;
b. providing a holding platform having a top, a bottom, and at least one chamber passing through said holding platform from said top to said bottom, with said at least one chamber including a top opening and a bottom opening;
c. separating said bottom of said holding platform from said bottom wall of said bubble reservoir;
d. covering said bottom opening of said at least one chamber with a screen;
e. filling said bubble reservoir with a preservation liquid to a level above said bottom of said holding platform but below said top of said holding platform, thereby flooding said at least one chamber to a level above said screen;
f. placing said biological specimen in said at least one chamber, said biological specimen having a density greater than said preservation liquid so that said biological specimen sinks to said screen covering said at least one chamber;
g. said level of said preservation fluid being sufficient to completely submerge said biological specimen;
h. forcing a gas including oxygen into said preservation liquid in said bubble reservoir, thereby producing a plurality of gas bubbles in said preservation liquid; and
i. wherein said screen has a mesh size small enough to prevent the passage of said plurality of gas bubbles.

16. A method of biological specimen preservation as recited in claim 15, wherein said mesh size is between about 0.10 mm and about 0.70 mm.

17. A method of biological specimen preservation as recited in claim 15, wherein said gas contains about 95% oxygen and about 5% carbon dioxide.

18. A method of biological specimen preservation as recited in claim 15, wherein:
a. said holding platform includes a plurality of chambers passing through said holding platform from said top to said bottom, with each of said chambers including a top opening and a bottom opening; and b. covering said bottom opening of each of said plurality of chambers with a screen.

19. A method of biological specimen preservation as recited in claim 15, further comprising attaching said gas diffuser to said bubble reservoir.

20. A method of biological specimen preservation as recited in claim 15, further comprising attaching said holding platform to said bubble reservoir.

* * * * *